Feb. 3, 1948. J. E. CRANE Plant Pat. 783
ROSE PLANT
Filed March 6, 1947
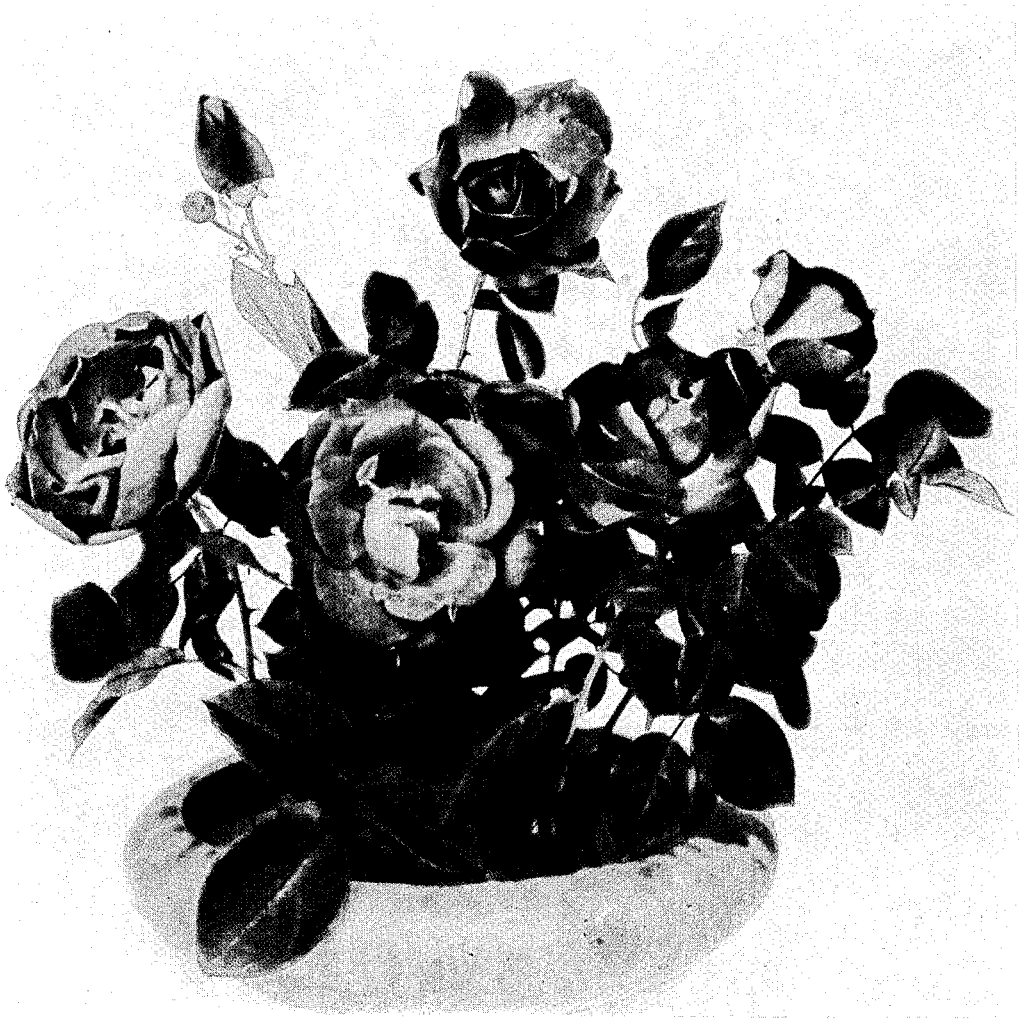
INVENTOR
Jasper E. Crane
By Orville M. Kile
Plant Patent Agt.

Patented Feb. 3, 1948

Plant Pat. 783

UNITED STATES PATENT OFFICE

783

ROSE PLANT

Jasper E. Crane, Wilmington, Del., assignor to
Edith C. Bosley, Mentor, Ohio

Application March 6, 1947, Serial No. 732,782

1 Claim. (Cl. 47—61)

My present discovery relates to a new and distinct variety of hybrid tea rose plant of the outdoor garden decoration type. It originated at my home in Wilmington, Delaware, as a sport of the Charles K. Douglas, and in many respects is like its parent, including the same habit of abundant bloom on sturdy plants. The principal difference is the darker color of the flower and the more velvety sheen of my variety.

This variety has been propagated by budding at West Grove, Pennsylvania, for several seasons, and its distinguishing characteristics appear to be firmly fixed.

The accompanying illustrations show a bowl of six specimens of the flowers of this new variety, together with portions of stems and foliage, all in approximately their true colors. Due allowance should be made for slight variation as between specimens and for the inability of the medium of water colors to show the velvety appearance.

Following is a detailed description of my new variety, with plate reference to Ridgway's Color Standards and Nomenclature whenever plate numbers are indicated. The description was made from roses grown outdoors in the month of October, at West Grove, Pennsylvania.

*The plant*

Growth habit: Vigorous, bushy, and upright.
Health: Resistant to mildew and blackspot.
Stems:
- *Canes.*—Moderately heavy.
- *Main stems and branches.*—Dull, strong, Elm Green (Pl. XVII).
- *New shoots.*—Bright Garnet Brown (Plate I).
- *Thorns.*—Several thorns are found on both main stems and branches. They are short, downward-hooked, and with round base. No prickles or hairs are evident.

Foliage:
- *Leaves.*—Compound, with 3 to 5 leaflets.
- *Quantity.*—Normal.
- *Size.*—Moderately large.
- *Shape.*—Leaflets linear with acute apex and obtuse base. Margin irregularly serrate.
- *Texture.*—Leathery.
- *Color.*—Mature foliage is Spinach Green (Plate V) on upper surface and Light Elm Green (Plate XVII) on under surface. Young foliage is Garnet Brown (Plate I) on upper surface and Light Garnet Brown (Plate I) on under surface.

Rachis: Medium in size. Upper side grooved and under side smooth.

Stipules: Short and narrow, with short points turning out at an angle of less than 45 degrees.

*The flower*

Borne: Singly, three or several to a stem in a pyramidal cluster, on long stems.
Quantity of bloom: Free blooming.
Continuity of bloom: Continuous bloomer.
Bud:
- *Before calyx breaks.*—Size—medium. Form—long pointed, with a conspicuous neck. Foliaceous appendages—foliaceous parts extend beyond tip of bud about the length of the bud itself.
- *As calyx breaks.* — Color — Oxblood Red (Plate I).
- *As first petal opens.*—Size—medium. Form—globular. Color—outside, Nopal Red (Plate I); inside, Oxblood Red (Plate I). Opening—opens well. Peduncle—erect, almost smooth, medium in length and weight, Biscay Green (Plate XVII). Sepals—permanent; moderately long.

Bloom:
- *Size.*—Medium. When fully open, the flower measures 4½ to 5 inches across.
- *Form.*—Open. At first loosely cupped, becoming flat. At maturity the petals are loosely rolled outward. Petals are arranged regularly.
- *Petalage.*—Semi-double, with 15 to 20 petals.
- *General color effect.*—Newly opened flower, Oxblood Red (Plate I). Flower open 3 days, Tyrian Rose (Plate XII).
- *Flower longevity.*—On bush in garden, flowers last 3 or 4 days in the month of October. Cut roses grown outdoors and kept at ordinary house temperatures last 4 or 5 days.

Petals:
- *Shape.*—Outer petals round, scalloped, with a point at tip. Intermediate and inner petals obovate.
- *Behavior.*—Drop off cleanly. Fade to Tyrian Rose (Plate XII).
- *Arrangement.*—Regular.
- *Texture.*—Thick.
- *Aspect.*—Inside very velvety. Outside satiny.

Color:
- *Newly opened flower.*—Outside surface Nopal Red (Plate I), with blackish edges; inside surface Oxblood Red (Plate I).
- *Opened three days.*—Outside surface Tyrian Pink (Plate XVII); inside surface Tyrian Rose (Plate XII).

Reproductive organs:

*Stamens.*—Many, arranged about pistils and mixed with petaloids. *Filaments*—short, Carrot Red (Plate XIV). *Anthers*—small, Salmon Buff (Plate XIV) and all open at one time. *Pollen*—moderate in quantity; buff yellow.

*Pistils.*—Medium number; bunched. *Styles*—medium in length and very slender. *Ovaries*—inclosed in calyx.

*Hips.*—Globular with inconspicuous neck.

Parrot Green (Plate VI): smooth; walls thin.

*Seeds.*—Many; medium sized.

Having thus disclosed my discovery, I claim:

The new and improved variety of hybrid tea rose plant, substantially as herein shown and described and essentially like its parent, Charles K. Douglas, except that it is characterized as to novelty by a flower of much darker color and more velvety sheen that intensifies its lustre.

JASPER E. CRANE.